US009138556B2

(12) United States Patent
Boussignac

(10) Patent No.: US 9,138,556 B2
(45) Date of Patent: Sep. 22, 2015

(54) DEVICE FOR RESPIRATORY ASSISTANCE, AND MEASUREMENT SYSTEM COMPRISING SUCH A DEVICE

(75) Inventor: Georges Boussignac, Antony (FR)

(73) Assignee: GEORGES BOUSSIGNAC, Antony (FR)

( * ) Notice: Subject to any disclaimer, the term of this patent is extended or adjusted under 35 U.S.C. 154(b) by 1357 days.

(21) Appl. No.: 12/581,530

(22) Filed: Oct. 19, 2009

(65) Prior Publication Data

US 2010/0258122 A1    Oct. 14, 2010

(30) Foreign Application Priority Data

Apr. 9, 2009   (FR) ..................................... 09 01752

(51) Int. Cl.
| | | |
|---|---|---|
| A61M 16/08 | (2006.01) | |
| A61M 16/00 | (2006.01) | |
| A61M 16/04 | (2006.01) | |
| A61M 16/12 | (2006.01) | |
| A61M 16/20 | (2006.01) | |

(52) U.S. Cl.
CPC ......... *A61M 16/085* (2014.02); *A61M 16/0003* (2014.02); *A61M 16/04* (2013.01); *A61M 16/08* (2013.01); *A61M 16/0816* (2013.01); *A61M 16/0858* (2014.02); *A61M 16/12* (2013.01); *A61M 16/127* (2014.02); *A61M 16/209* (2014.02); *A61M 2016/0027* (2013.01); *A61M 2230/432* (2013.01)

(58) Field of Classification Search
CPC . A61M 16/00; A61M 16/0003; A61M 16/04; A61M 16/0402; A61M 16/0413; A61M 16/0411; A61M 16/465
USPC ............ 128/204.22, 204.18, 204.23, 204.24, 128/205.23, 200.24, 202.27, 203.12, 128/203.15, 203.14, 207.14–18
See application file for complete search history.

(56) References Cited

U.S. PATENT DOCUMENTS

| | | | |
|---|---|---|---|
| 5,291,882 A | | 3/1994 | Makhoul |
| 5,954,050 A | | 9/1999 | Christopher |
| 6,152,132 A | * | 11/2000 | Psaros ....................... 128/204.25 |
| 8,443,797 B2 | * | 5/2013 | Hauge ....................... 128/200.26 |
| 2002/0108610 A1 | * | 8/2002 | Christopher ............. 128/200.26 |
| 2003/0159696 A1 | | 8/2003 | Boussignac |
| 2004/0050389 A1 | * | 3/2004 | Boussignac .............. 128/207.14 |
| 2008/0105263 A1 | | 5/2008 | Jadhav |

FOREIGN PATENT DOCUMENTS

EP    1 340 515    9/2003

OTHER PUBLICATIONS

French Search Report dated Nov. 5, 2009 with English translation.

* cited by examiner

*Primary Examiner* — Justin Yu
*Assistant Examiner* — Colin W Stuart
(74) *Attorney, Agent, or Firm* — Dickinson Wright PLLC

(57) ABSTRACT

Disclosed is a device for respiratory assistance and a measurement system that includes the device. The device includes a tube, which forms a main channel, and at least one auxiliary channel connected to a source of respiratory gas. The device further includes a unit by which vitiated gas, exhaled by a patient, is removed from the patient between a distal end of the auxiliary channel, which opens into the main channel, and a distal end of the main channel, and which is configured to capture and remove the exhaled gas, undiluted by insufflated fresh respiratory gas.

3 Claims, 3 Drawing Sheets

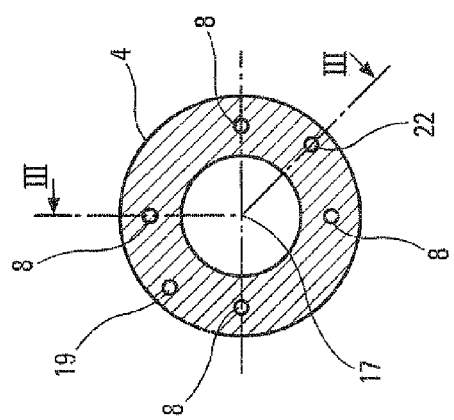
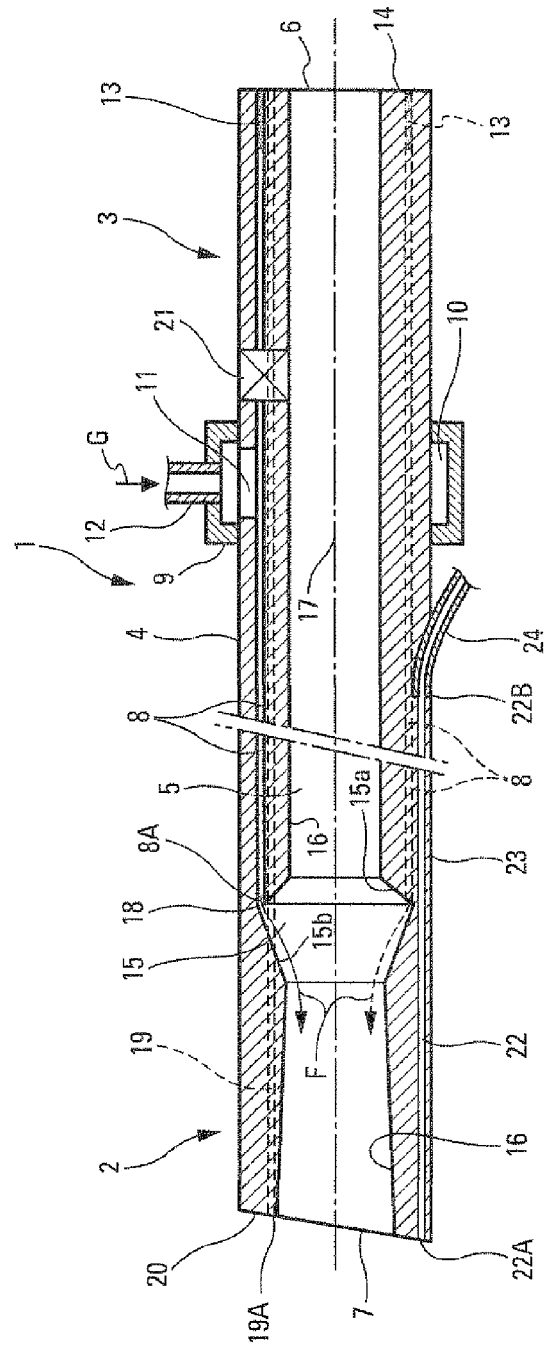

DEVICE FOR RESPIRATORY ASSISTANCE, AND MEASUREMENT SYSTEM COMPRISING SUCH A DEVICE

FIELD OF THE INVENTION

The subject of the present invention is a device for respiratory assistance that can be used on patients in whom spontaneous respiration is absent or inadequate, whether or not the patients are placed under artificial respiration. The invention moreover relates to a system for measuring at least one parameter of the vitiated gas exhaled by the patients.

BACKGROUND OF THE INVENTION

Various devices for respiratory assistance are known, such as oral, nasal, endotracheal and tracheotomy probes and cannulas, which are designed to form the junction between an artificial respiration and/or anesthesia apparatus and the respiratory system of a patient.

Depending on the circumstances, these devices comprise a tube which forms a main channel designed to be connected, via its distal end, to an airway of a patient such that this main channel connects the respiratory system of the patient to the outside, the device often comprising at least one auxiliary channel which, for example, is formed in the wall of said tube and is connected to a source of respiratory gas, so as to permit the injection of a constant or pulsed jet of respiratory gas (oxygen, air or a mixture of air and oxygen) intended to ventilate the patient, this auxiliary channel opening into the main channel in the vicinity of the distal end of the latter.

It is also known that, when using such a device on a patient in cardiac arrest, the restarting of the heart by cardiac massage can be detected by measuring the partial pressure of carbon dioxide EtCO2 (end-tidal CO2) in the vitiated air exhaled by the patient by means of an analyzer, for example a capnometer. EtCO2 is a parameter that is dependent on two important vital functions of the body, namely ventilation and blood flow, such that it provides a simple reflection of the efficacy of the cardiac massage. Thus, it is known to analyze the vitiated air exhaled by the patient at the outlet of the proximal end of the respiratory assistance device in such a way as to determine the presence of EtCO2 and thereby detect a possible restart of the patient's heart.

However, the vitiated air emerging from such a respiratory device is generally diluted by respiratory gas introduced into the main channel by way of the auxiliary channel(s). It then often happens that the small quantity of EtCO2 present in the vitiated air, and representative of the onset of the restart of the heart, is so diluted that it is not detected by the capnometer. Therefore, the operators manipulating the device for artificial respiration are alerted to the restart of the heart only when the quantity of EtCO2 in the diluted vitiated gas exceeds a certain detection threshold (the heart by then having already been restarted for some moments). They therefore continue to perform the cardiac massage, which involves alternate compression and decompression exerted on the thoracic cage of the patient, at least until they are informed of the restart of the heart.

However, if this cardiac massage is performed over a prolonged period, it frequently produces, in the patient's lungs, lesions that may cause bleeding.

It is therefore preferable if the restart of the heart is indicated as soon as possible to the operators, such that they stop massaging the thoracic cage of the patient as early as possible and provide other and more appropriate care.

SUMMARY OF THE INVENTION

The object of the present invention is to overcome this disadvantage and, in particular, to permit rapid detection of the restart of the heart of a patient in a state of cardiac arrest.

To this end, according to the invention, the device for respiratory assistance, comprising a tube which forms a main channel designed to be connected, via its distal end, to an airway of a patient such that said main channel connects the respiratory system of said patient to the outside, said device comprising at least one auxiliary channel which is connected to a source of respiratory gas, so as to be able to insufflate a jet of such a respiratory gas into said respiratory system, and which opens, via its distal end, into said main channel in the vicinity of the distal end of the latter, is characterized in that it comprises means by which vitiated gas, exhaled by said patient, is removed between the distal end of said auxiliary channel and the distal end of said main channel.

Thus, by virtue of the invention, the vitiated gas exhaled by the patient and removed by the removal means is not diluted, or is only very slightly diluted, by fresh respiratory gas originating in particular from the auxiliary channel or channels connected to the source of respiratory gas. Consequently, when these removal means are connected to standard means for measuring the partial pressure of EtCO2 (for example a capnometer), it is possible to detect and measure very small quantities of EtCO2, which would be undetectable in vitiated air diluted by respiratory gas.

In the case of a patient in a state of cardiac arrest, the operators can therefore be alerted immediately, or almost immediately, to the restart of the heart, and this allows them to react quickly and to provide the appropriate care to the patient.

Said means for removing undiluted vitiated gas are preferably in the form of at least one removal channel.

The latter can advantageously be formed within the thickness of the wall of said tube and can extend along at least part of the length of the latter.

The distal end of said removal channel is advantageously arranged between the distal end of said auxiliary channel and the distal end of said main channel, such that the vitiated gas that is removed is not diluted, or is only very slightly diluted, by fresh respiratory gas.

Furthermore, means for deflecting said jet of respiratory ventilation gas toward the axis of said main channel can be provided opposite the distal orifice of said auxiliary channel, and the distal end of said removal channel is arranged between said means of deflection and said distal end of said main channel.

The invention also relates to a system for measuring at least one parameter of the vitiated gas exhaled through an airway of a patient, said patient being under respiratory assistance with the aid of a device for respiratory assistance comprising a tube which forms a main channel designed to be connected, via its distal end, to said airway of the patient such that said main channel connects the respiratory system of said patient to the outside, said device comprising at least one auxiliary channel which is connected to a source of respiratory gas, so as to be able to insufflate a jet of such a respiratory gas into said respiratory system, and which opens, via its distal end, into said main channel in the vicinity of the distal end of the latter.

According to the invention, said device comprises means by which vitiated gas, exhaled by the patient, is removed between the distal end of said auxiliary channel and the distal end of said main channel; and said system additionally comprises means for measuring said parameter of the vitiated gas exhaled by the patient.

Moreover, said means for removal of vitiated gas are preferably in the form of at least one removal channel formed within the thickness of the wall of said tube and extending along at least part of the length of the latter, the distal end of said removal channel being arranged between the distal end of said auxiliary channel and the distal end of said main channel.

In addition, said system can comprise a hollow tubular endpiece designed to be attached to the proximal end of said tube, said tubular endpiece comprising a protruding lateral connector element not communicating with the inner space of said endpiece.

Furthermore, said system can advantageously comprise a hollow connector designed to be attached, at one of its ends, to said protruding lateral element of said tubular endpiece. In addition, said removal channel is designed to be connected, via its proximal end, to another end of said connector. The latter can comprise a lateral nozzle communicating with the inner space of said connector and designed to be connected to said measuring means.

BRIEF DESCRIPTION OF THE DRAWINGS

Preferably, said parameter is the partial pressure of carbon dioxide, and said measuring means form a capnometer.

The figures in the attached drawing will show clearly how the invention can be achieved. In these figures, identical references designate like elements.

FIG. 2 is a schematic cross section of the device from FIG. 1 along the line II-II.

FIG. 3 is a partial schematic view of the device for respiratory assistance according to the present invention, in an enlarged axial section along the line III-III in FIG. 2.

DETAILED DESCRIPTION OF THE INVENTION

Figure 1:
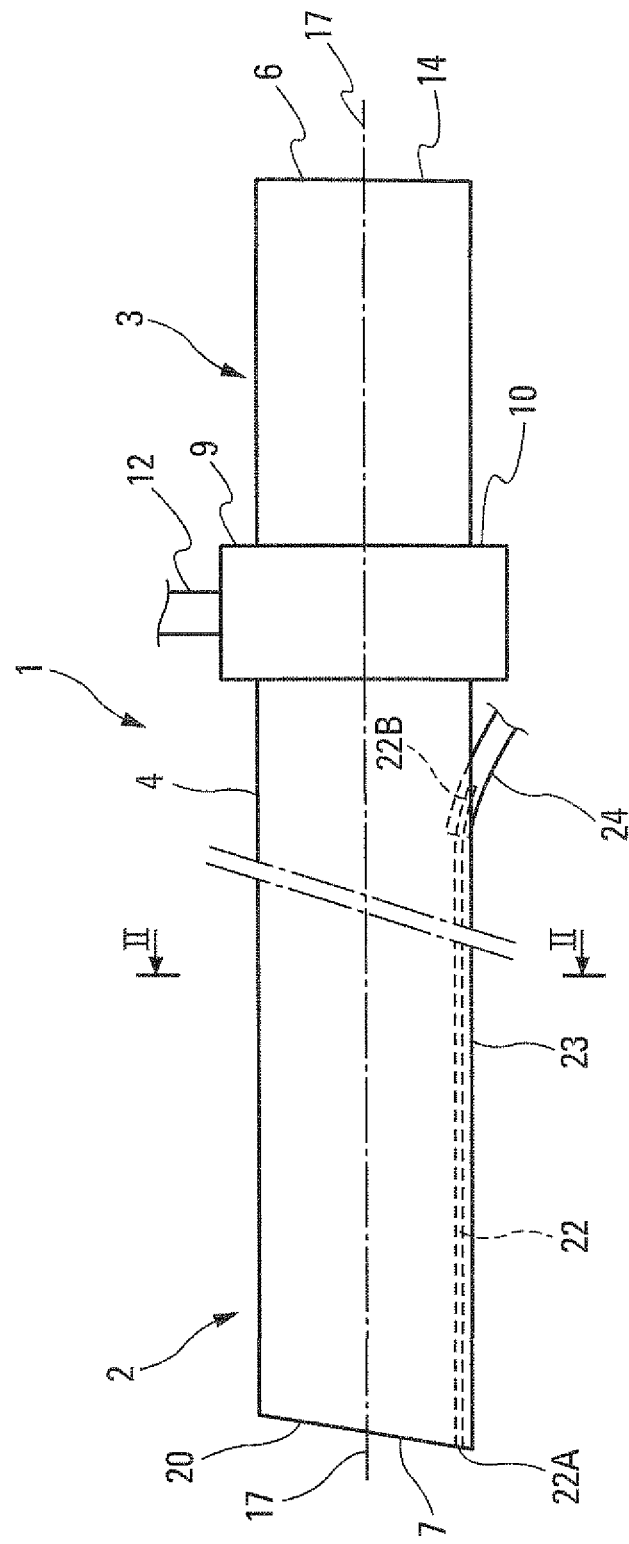
FIG. 1 is a partial schematic side view of an embodiment of the device for respiratory assistance according to the present invention.

FIG. 1 shows, schematically and on a large scale, only the proximal portion 3 and distal portion 2 of an embodiment of the device 1 for respiratory assistance according to the present invention. This device 1 can constitute, for example, an oronasal endotracheal probe with or without balloon, a pediatric endotracheal probe, a probe for gas monitoring, an endobronchial probe, an anatomical intubation probe for children, a Cole neonatal probe, a Gedel cannula probe, a nasal probe for oxygen therapy, a nasal or bucconasal mask or a nasal balloon for treatment of sleep apnea.

As is shown in FIGS. 2 and 3, the device 1 comprises a tube 4 which is flexible or pre-shaped (to adapt to the morphology of the patient) and which delimits a main channel 5 having a proximal orifice 6 and a distal orifice 7 respectively at the ends of said tube 4.

Thus, the main channel 5 is capable of ensuring a passage between the proximal orifice 6 and distal orifice 7, one of which (distal orifice 7) is intended to be located within the airways of a patient, while the other (proximal orifice 6) is intended to be located outside said patient. This proximal orifice 6 can open to the ambient air, and in this case the patient can inhale fresh air and exhale vitiated air through the main channel 5. As is explained below, it is also possible to connect the orifice 6 to a source of respiratory gas under pressure and to provide a system of unidirectional valves, such that the patient inhales the respiratory gas from said source via said main channel 5 and exhales the vitiated gas to the ambient air, again via this main channel 5.

The diameter of the main channel 5 is of the order of a few millimeters. Satisfactory trials have been carried out with diameters of 3 mm, 7 mm, 8 mm and 12 mm.

Moreover, auxiliary channels 8 are formed within the thickness of the wall of the tube 4, said auxiliary channels 8 extending along almost the entire length of the main channel 5 and being designed to be connected to a source of respiratory gas under pressure, as is described below.

The connection to the source of respiratory gas can be effected by means of a ring 9, surrounding the tube 4 in a leaktight manner toward the proximal portion 3 and delimiting a sealed annular chamber 10 around said tube 4. The auxiliary channels 8 are brought into communication with the annular chamber 10 by means of local cutouts 11 in the wall of the tube 4, and said chamber 10 is connected to said source of respiratory gas via a conduit 12. Of course, the proximal ends of the channels 8 are closed off, for example by stoppers 13 introduced from the proximal end face 14 of the tube 4.

The auxiliary channels 8 have a diameter smaller than that of the main channel 5. The diameter of the auxiliary channels 8 is preferably less than 1 mm and is advantageously of the order of 5 to 800 microns. At the distal end 8A, the auxiliary channels 8 open into a deflector including a recess 15 of the inner wall 16 of the tube 4. The recess 15 is annular and centered on the axis 17 of said tube 4. The deflector further comprises a face 15a, which is substantially transverse or slightly inclined in such a way as to constitute a widening of the main channel 5 into which said auxiliary channels 8 open via their orifices 18, and also a face 15b following the face 15a and converging in the direction of the axis 17.

Thus, when the auxiliary channels 8 are supplied with respiratory gas under pressure (arrow G in FIG. 3) by way of the elements 9 to 12, the corresponding gaseous jets impact flow to the inclined face 15b of the deflector, which deflects them in the direction of the axis 17 (arrows F in FIG. 3), generating in the vicinity thereof a pressure zone that promotes the circulation of gas inside the main channel 5, from the proximal orifice 6 to the distal orifice 7. This promotes the patient's inhalation.

At least one supplementary channel 19 is provided within the thickness of the tube 4 and opens out at 19A in the vicinity of the distal end face 20 of the tube 4 and serves as a pressure tap.

For safety reasons, a calibrated exhaust valve 21 can be provided in the proximal portion 3 of the tube 4. Thus, in the event of an accidental overpressure in the main channel 5, gas escapes to outside the patient, via the wall of the tube 4, in order to eliminate this overpressure instantaneously.

As is shown in FIG. 2, the auxiliary channels 8 are arranged regularly around the axis of the tube 4. Their number varies depending on the application (adult or child), but it is generally between three and nine. Moreover, at least one of the auxiliary channels 8 can be specialized to deliver a medical fluid.

The tube 4 of the device 1 according to the invention can be made of any material already used in respiratory probes, for example polyvinyl chloride, with an optional coating of silicone or steel permitting high-pressure injections.

Of course, the dimensions of the device 1 according to the invention can vary greatly, essentially depending on the mode of fitting of the tube and the size of the patient, who can be an adult, a child, an infant or a premature baby.

In addition, as is shown in FIGS. 1 to 3, a channel 22 for removing vitiated gas, which is exhaled by the patient and is not diluted by the respiratory gas originating from the auxiliary channels 8, is formed within the thickness of the wall of the tube 4 and extends along part of the length of the latter.

The distal end 22A of the removal channel 22 opens out in the distal end face 20 of the tube 4. Of course, as an alternative, the distal end 22A of the removal channel 22 could open into the outer wall 23 and/or into the inner wall 16 of the tube 4, between the distal end 7 of the latter and the outlet orifice 18 of the auxiliary channels 8.

The removal channel 22 is continued outside the tube 4, for example by a tube 24 which is attached to the outer wall 23 of said tube 4, in the area of the proximal end 22B of the channel 22, arranged in front of the ring 9 surrounding the tube 4.

Figure 4:
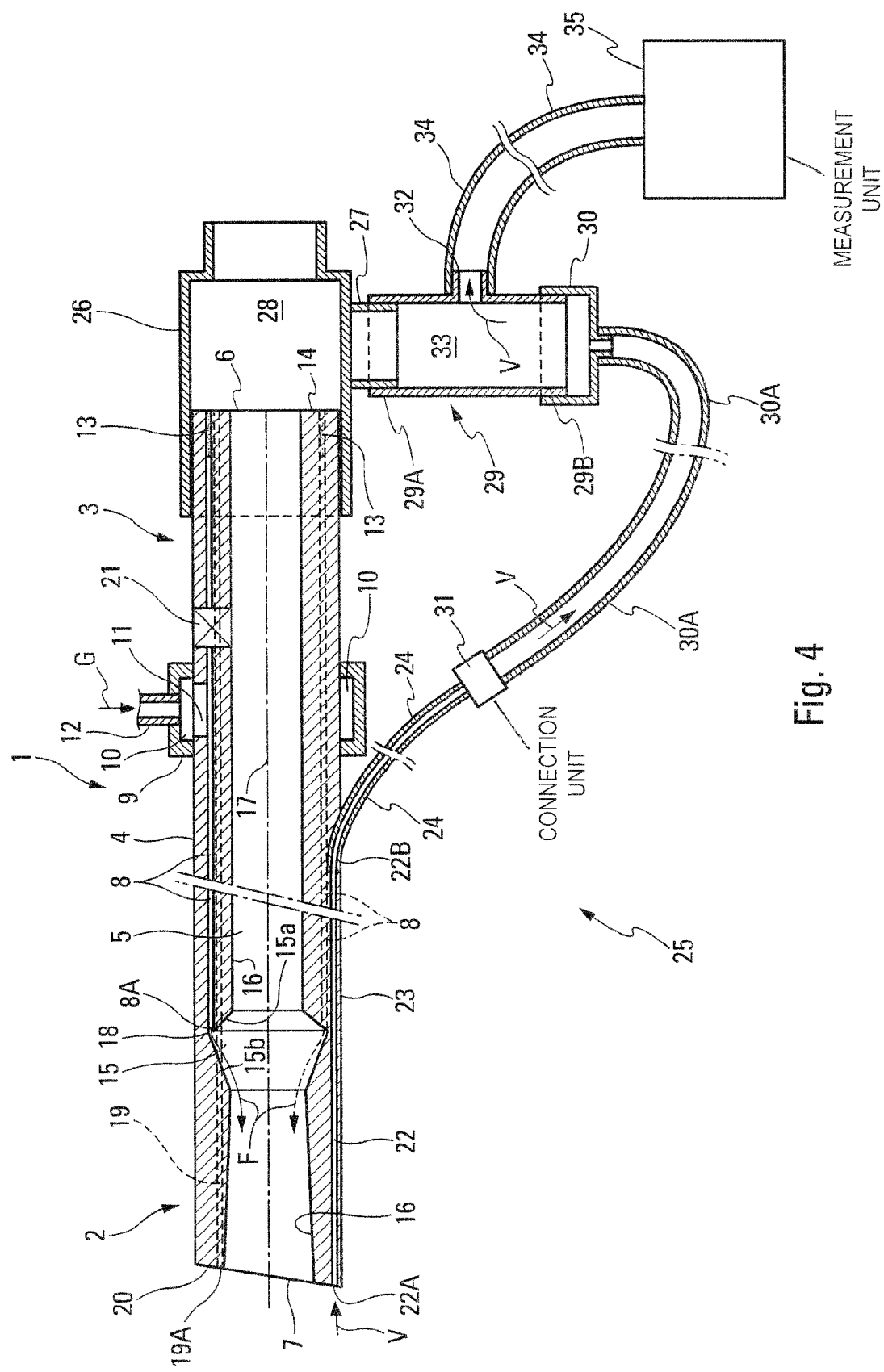
FIG. 4 shows, in a view similar to FIG. 3, an example of the measurement system according to the present invention, using the device for respiratory assistance from FIG. 1.

Moreover, FIG. 4 shows an example of a system 25 according to the invention for measuring the partial pressure of carbon dioxide EtCO2, using the aforementioned device for respiratory assistance 1 (FIGS. 1 to 3).

A hollow tubular endpiece 26 can be attached movably or immovably to the proximal end 6 of the tube 4, such that it forms a continuation of the latter. This endpiece 26 comprises a protruding lateral connector element 27, which does not communicate with the inner space 28 of said endpiece 26.

A hollow tubular connector 29 in the shape of a T, comprising two opposite ends 29A and 29B, can be connected to the lateral element 27 of the endpiece 26 via the end 29A. The other end 295 of the connector 29 can be connected, for example movably, to a connecting endpiece 30, which is itself connected to a conduit 30A.

The tube 24 continuing the removal channel 22 of the device 1 can be connected to the conduit 30A by connecting means 31.

The tubular connector 29 additionally comprises a lateral nozzle 32 which is in communication with the inner space 33 of said connector 29. It can be connected, by way of a tube 34, to a device 35 for measuring the partial pressure of exhaled carbon dioxide EtCO2 (for example a capnometer).

Thus, the measurement system functions as follows. The removal channel 22, at its distal end 22A, removes vitiated gas (arrow V) exhaled by the patient but not diluted by fresh respiratory gas (arrow F). This undiluted vitiated gas, once removed, is conveyed to the measurement device 35 for analysis, by way of the removal channel 22, the tube 24, the conduit 30A, the inner space 33 and the tube 34.

The invention claimed is:

1. A system for measuring at least one parameter of an exhaled gas exhaled through an airway of a patient under respiratory assistance, said system comprising
 a) a device for respiratory assistance, said device comprising:
  i) a tube having a wall, which forms a main channel, and is configured for connecting, via a distal end of the main channel and the tube, to an airway of a patient such that said main channel connects the patient's respiratory system to ambient air outside of the patient;
  ii) at least one auxiliary channel connected to a source of fresh respiratory gas, and configured for insufflating a jet of said fresh respiratory gas into said patient's respiratory system, wherein said at least one auxiliary channel opens, via a distal end, into said main channel at a vicinity of the distal end of the main channel and the tube; and
  iii) at least one capture and removal channel by which exhaled gas, exhaled by said patient, is captured and removed from the patient, with said at least one capture and removal channel being configured to capture and remove the exhaled gas, undiluted by the insufflated fresh respiratory gas, wherein said at least one capture and removal channel is formed within a thickness of the wall of said tube and extends along a length of the tube, and a distal end of the at least one capture and removal channel opens out at a distal end face of the tube;
 b) a measurement unit for measuring said at least one parameter of the exhaled gas exhaled by the patient;
 c) a hollow tubular end piece configured for attaching to a proximal end of said tube, wherein said hollow tubular end piece defines an inner space and comprises a protruding lateral connector element not communicating with the inner space of said end piece; and
 d) a hollow connector, configured for attaching to said protruding lateral connector element of said hollow tubular end piece,
wherein:
said at least one capture and removal channel is configured for connecting, via a proximal end, to another end of said hollow connector; and
said hollow connector defines an inner space and comprises a lateral nozzle communicating with the inner space of said hollow connector and is configured for connecting to said measurement unit.

2. The system as claimed in claim 1, wherein
said at least one parameter is partial pressure of carbon dioxide; and
said measurement unit forms a capnometer.

3. The system as claimed in claim 1, wherein, in the device for respiratory assistance, a deflector for deflecting said jet of fresh respiratory gas toward an axis of said main channel is provided opposite the distal end of said at least one auxiliary channel.

* * * * *